US00PP08070P

United States Patent [19]

Zaiger et al.

[11] Patent Number: Plant 8,070

[45] Date of Patent: Dec. 22, 1992

[54] PEACH TREE "SUMMER SWEET"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95351

[21] Appl. No.: 716,673

[22] Filed: Jun. 17, 1991

[51] Int. Cl.[5] ..... A01H 5/00

[52] U.S. Cl. ..... Plt./42.1

[58] Field of Search ..... Plt./40.1, 42.1

[56] References Cited

U.S. PATENT DOCUMENTS

P.P. 6,806 5/1989 Taylor ..... Plt. 40

OTHER PUBLICATIONS

Childers, N. F., *Modern Fruit Science* (1969) Horticultural Publications Rutgers University, p. 833.

Anon, *International Code of Nomenclature for Cultivated Plants*—1980 (1980) Bohn, Scheltema & Holkema, Utrecht dr. W. Junk b.v. Publishers, The Hague, p. 24.

*Primary Examiner*—James R. Feyrer

[57] ABSTRACT

The present discovery is a distinct variety of peach tree which has the following unique combination of desirable features that are outstanding in a new variety:

1. Fruit with very firm white flesh having good storage and shipping qualities.
2. Heavy and regular production of fruit.
3. Fruit with large size.
4. Fruit with excellent flavor and eating quality.
5. Fruit with a high degree of attractive red skin color.
6. Coloring of fruit 7 to 10 days before ripening.

1 Drawing Sheet

ORIGIN OF THE VARIETY

The new and distinct variety of peach tree was originated by use in our experimental orchard located near Modesto, Calif., as a first generation cross between two selected seedlings with the field identification Nos. 23R236 and 44EB108. The material parent with the field identification No. 23R236 originated as a second generation seedling from a cross between two selected seedlings, one a peach of unknown parentage and the other originated from a cross between O'Henry Peach (U.S. Plant Pat. No. 2,964) and Giant Babcock Peach (U.S. Plant Pat. No. 1,353). The parental parent 44EB108 originated as a second generation seedling from a cross between Redwing Peach (U.S. Plant Pat. No. 621) and a very firm, high colored, early maturing nectarine of unknown parentage. A large group of seedlings, which were planted and grown by use, gave many and varying characteristics. One such seedling, which is the present variety, evidenced distinctive desirable fruit characteristics and was selected for asexual reproduction and commercialization.

ASEXUAL REPRODUCTION OF THE VARIETY

The present new variety of peach tree was asexually reproduced by budding, as performed by us in our experimental orchard located near Modesto, Calif. and shows that all characteristics of the tree and its fruit are established and transmitted through succeeding propagations and come true to the original tree in all respects.

SUMMARY OF THE VARIETY

The new and distinct variety of peach tree is of large size, vigorous upright growth; the tree being a regular and productive bearer of large size, white flesh, freestone fruit with excellent flavor and eating quality. The fruit is further characterized by having an attractive red skin color, being of firm flesh with good storage and shipping qualities and in comparison to the two white flesh parents in its genetic background, Giant Babcock Peach (U.S. Plant Pat. No. 1,353) and Redwing Peach (U.S. Plant Pat. No. 621), the new variety has a higher degree of attractive red skin color and also has firmer flesh with greater handling and shipping qualities.

PHOTOGRAPHS OF THE VARIETY

The accompanying photographic illustrations show typical specimens of the foliage and fruit of our new peach variety, with an exterior and sectional view of the fruit to show pit cavity, flesh coloration and a stone remaining in place. A small section of a branch and foliage, with the upper and lower surface of the leaves, is illustrated. The photographs were taken shortly after being picked (firm ripe) and the colors are as nearly true as is reasonably possible in a color representation of this type.

DESCRIPTION OF THE VARIETY

The following is a detailed botanical description of the flowers, foliage and fruit of our new peach variety, as based on observations of the variety grown in our experimental orchard located near Modesto, Calif., with color terminology (except those in common terms) in accordance with Reinhold Color Atlas by A. Kornerup and J. H. Wanscher.

Tree:

*Size.*—Large.
*Vigor.*—Vigorous.
*Growth.*—Upright.
*Density.*—Medium.
*Shape.*—Pruned to vase shape.
*Productivity.*—Productive.
*Bearer.*—Regular.

Trunk:

*Size.*—Medium stocky.
*Texture.*—Medium shaggy.
*Color.*—Brown to grayish brown (5-E-4) to (5-E5).

Branchs:

*Size.*—Medium.

*Texture.*—Smooth to medium rough.

*Lenticels.*—Numerous. Medium size.

*Color.*—Brown to reddish brown (8-D-5) to (8-D-8).

Leaves:

*Size.*—Large. Average length — $6\frac{1}{4}''$ to $6\frac{1}{2}''$. Average width — $1\frac{1}{4}''$ to $1\frac{1}{2}''$.

*Texture.*—Smooth.

*Petiole.*—Medium length. Medium thickness.

*Form.*—Lanceolate. Acutely pointed.

*Margin.*—Crenate.

*Glands.*—Reniform. Number varies from 2 to 6. Average number 3. Positioned on lower portion of leaf blade and upper portion of petiole.

Flower buds:

*Size.*—Medium to large.

*Form.*—Plump.

*Pubescence.*—Pubescent.

Flowers:

*Size.*—Large — showy.

*Blooming period.*—Date of first bloom — Feb. 25, 1990. Date of last bloom — Mar. 5, 1990. Varies slightly with climatic conditions.

*Pollen.*—Present. Self fertile.

*Color.*—Pink.

Fruit:

*Maturity when described.*—Firm ripe.

*Date of first picking.*—Jul. 5, 1990.

*Date of last picking.*—Jul. 10, 1990.

*Size.*—Large. Average diameter axially — 3". Average transversely in suture plane .— 3".

*Form.*—Globose — nearly symmetrical.

*Suture.*—Very shallow — nearly rounded, extends from base to apex.

*Ventral surface.*—Usually rounded.

*Cavity.*—Rounded to slightly elongated in suture plane. Average depth — $\frac{1}{2}''$. Average breadth — 1".

*Base.*—Retuse.

*Apex.*—Usually rounded, varies from very slight tip to slight depression.

Skin:

*Thickness.*—Medium.

*Texture.*—Medium — tenacious to flesh.

*Tendency to crack.*—None.

*Down.*—Moderate amount, short to very short in length.

*Color.*—White to yellowish white ground color (3-A-1) to (3-A-2). Overspread with lake red to garnet red (9-C-8) to (9-D-8).

Flesh:

*Ripen.*—Evenly.

*Texture.*—Very firm.

*Fibers.*—Few, small, tender.

*Juice.*—Moderate.

*Aroma.*—Moderate.

*Amygdalin.*—Undetected.

*Flavor.*—Excellent, sub-acid, mild, sweet.

*Eating quality.*—Excellent.

*Color.*—White to oyster shell white (2-A-1) to (2-A-2). Pit cavity red to high red (10-A-6) to (10-A-7) with slight bleeding of red into flesh around pit cavity.

Stone:

*Type.*—Freestone.

*Size.*—Large. Average length — $1\frac{3}{8}''$. Average width — 1 1/16". Average thickness — $\frac{5}{8}''$.

*Form.*—Oval to obovate.

*Base.*—Usually rounded, some straight.

*Apex.*—Acuminate.

*Surface.*—Irregularly furrowed toward apex, pitted toward base. Pits vary from elongated to round.

*Ridges.*—Usually round.

*Sides.*—Equal to unequal, ventral surface thin.

*Tendency to split.*—Very slight.

*Color.*—Reddish brown to brown (9-D-5) to (9-E-5).

Use: Dessert. Local and long distance markets.

Keeping Quality: Good.

Shipping quality: Good.

The new and distinct peach tree, its flowers and fruit may vary in slight detail due to climatic conditions, soil type and cultural practices under which the variety may be grown; the present description is that of the new variety grown under the ecological conditions prevailing near Modesto. Calif.

The following is claimed:

1. A new and distinct variety of peach tree, substantially as illustrated and described, characterized by its large size, vigorous upright growth and being a regular and productive bearer of large, very firm, white flesh, freestone fruit with excellent flavor and eating quality; the fruit is further characterized in comparison to the white flesh varieties Giant Babcock Peach (U.S. Plant Pat. No. 1,353) and Redwing Peach (U.S. Plant Pat. No. 621) as having a higher degree of attractive red skin color, firmer flesh with greater handling and shipping qualities.

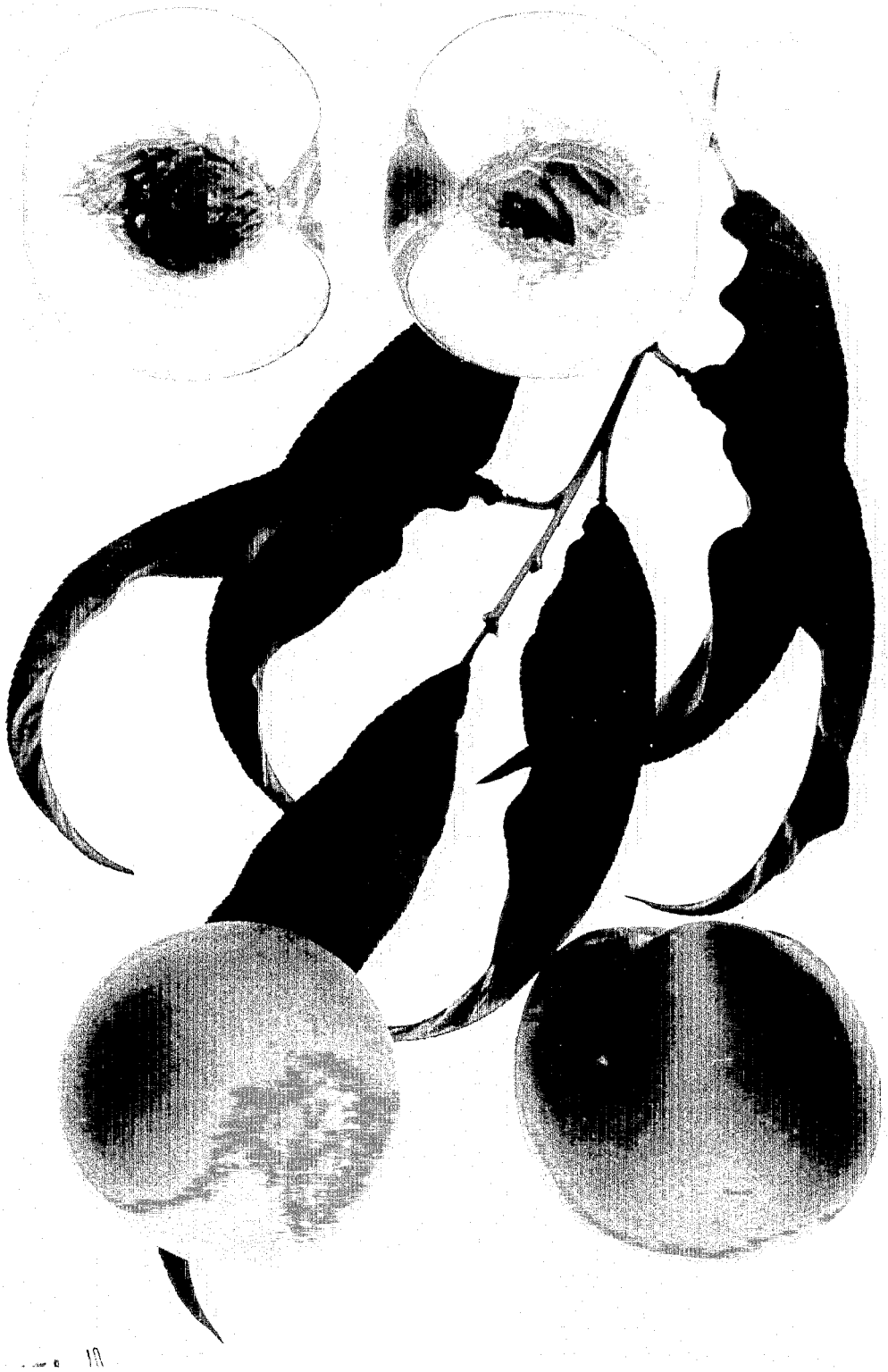

* * * * *